Figure 1:
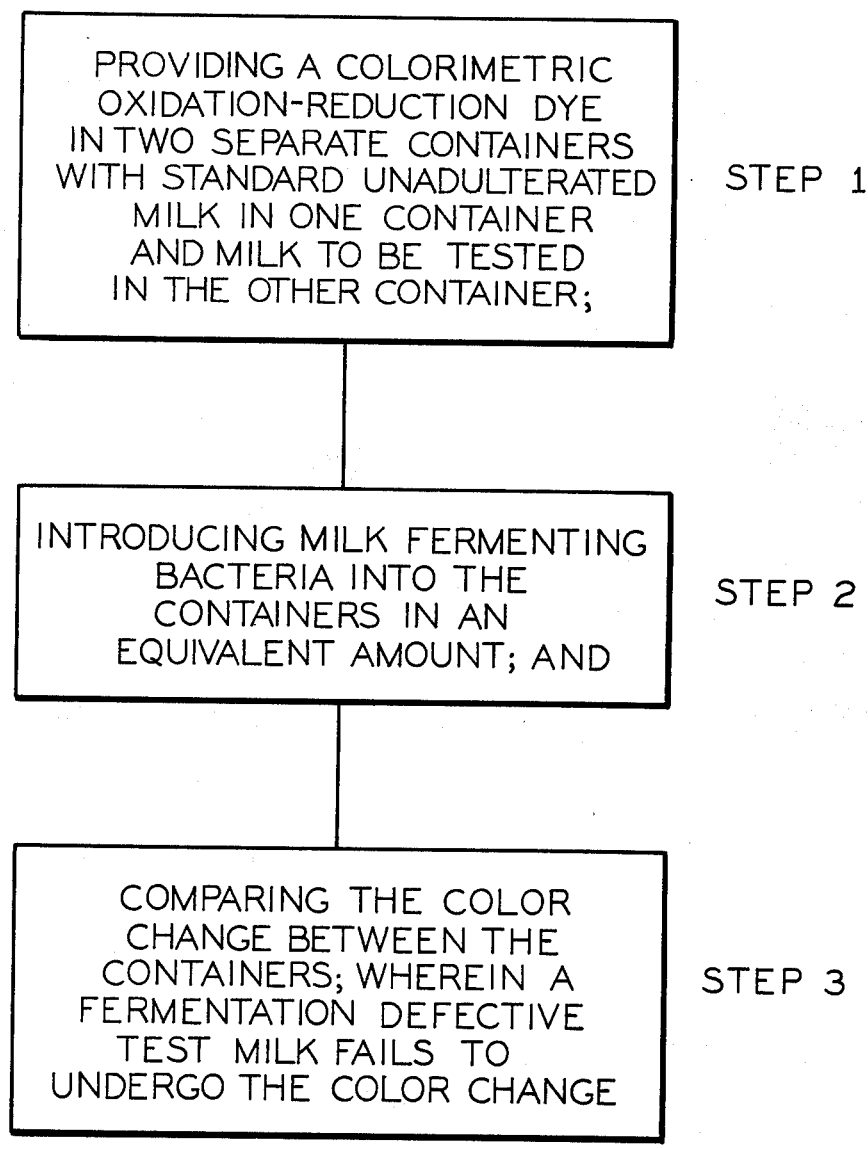

United States Patent [19]

Vedamuthu

[11] 3,963,580

[45] June 15, 1976

[54] METHOD FOR DETERMINING THE SUITABILITY OF MILK FOR BACTERIAL FERMENTATION ACTIVITY

[75] Inventor: Ebenezer R. Vedamuthu, Bradenton, Fla.

[73] Assignee: Microlife Technics, Inc., Sarasota, Fla.

[22] Filed: Feb. 10, 1975

[21] Appl. No.: 548,239

[52] U.S. Cl. .............................. 195/103.5 R; 426/34
[51] Int. Cl.² ............................................. C12K 1/04
[58] Field of Search ................. 195/103.5 R; 426/34

[56] References Cited
OTHER PUBLICATIONS

American Public Health Association; *Standard Methods for Examination of Dairy Products*; 13th Edition; 1972.

*Primary Examiner*—A. Louis Monacell
*Assistant Examiner*—Robert J. Warden
*Attorney, Agent, or Firm*—Miller, Morriss, Pappas & McLeod

[57] ABSTRACT

A method for testing milk to determine its ability to be fermented by bacteria in order to produce cheese, cottage cheese and the like is described. The method utilizes a colorimetric oxidation-reduction dye which rapidly changes color when the milk is readily fermentable.

10 Claims, 1 Drawing Figure

3,963,580

METHOD FOR DETERMINING THE SUITABILITY OF MILK FOR BACTERIAL FERMENTATION ACTIVITY

SUMMARY OF INVENTION

The present invention relates to a colorimetric test method designed to rapidly and easily determine the suitability of milk for good growth and acid production by starter bacteria. The invention particularly relates to a test method utilizing standard colorimetric oxidation-reduction dyes and a sterilized standard milk.

PRIOR ART

In the prior art colorimetric oxidation-reduction indicator dyes are used in a test to determine the grade of raw or whole milk. The test results depend upon the utilization of oxygen present in the raw milk by resident bacteria which reduce the oxidation-reduction potential of the milk producing a color change in the dye. Rapid reduction of the indicator dye is an indication of a high bacterial count and thus a poor grade milk. Bacteria are present in the milk because of contamination or because they are naturally occurring in the milk. The purpose of this test is thus to show that the milk is relatively low in bacterial count and therefore is of a high grade. The method is described in Chapter 15 of Standard Methods For Examination of Dairy Products (13th Edition 1972, Published by American Public Health Association, Washington, D.C.).

In the making of cultured milk products, such as cheese and buttermilk and the like, large quantities of milk are used. This milk, sometimes called vat milk in the cheese making arts, may be processed, usually in the culturing plant, for the removal of fats, usually using cream separators. In some instances, the milk may be heat-treated.

Bacterial concentrates containing between about $10^9$ to $10^{11}$ cells per ml are used to ferment milk and are usually purchased from a supplier by the dairy. Also used are "starter cultures" which are maintained in the dairies. In both instances, there are certain milks which will retard or completely inhibit the growth of some or all of the fermentation bacteria and which should not be used for this purpose. The problem in the past is that the dairies have had to throw away very large batches of milk which could not be readily fermented or "set" by adding starter bacteria.

OBJECTS

It is therefore an object of the present invention to provide a method to rapidly and easily determine the suitability of milk for good growth and acid production by starter bacteria prior to the introduction of the starter to the bulk of the milk. It is further an object of the present invention to provide a method whereby large amounts of milk can be saved from fermentation failures.

These and other objects will become increasingly apparent by reference to the following description and to the drawing.

IN THE DRAWING

FIG. 1 is a schematic diagram of the test method of the present invention.

The present invention relates to the method of determining the bacterial fermentation activity of skim milk by using a colorimetric oxidation-reduction sensitive dye, which comprises providing the colorimetric dye in at least two separate sterile openable and resealable containers and a standard unadulterated sterile skim milk in one container and a milk to be tested in the other container; introducing milk fermenting bacteria into the containers in an equivalent amount; and comparing the color change between the containers, wherein a fermentation defective milk is determined by a failure of the test milk to rapidly undergo the color change in relation to the color change in the standard milk container.

Preferably there should be at least about $1 \times 10^5$ cells per ml used for the test. The minimum number which will give a positive result within 1 to 3 hours is preferred to prevent the masking effects of overwhelming number of cells and thus between about $1 \times 10^5$ and $1 \times 10^8$ cells per ml of the bacterium are preferably used.

The present method is designed to rapidly and easily determine the suitability of vat or skim milk for good growth of starter bacteria. There are several inherent factors in milk, as it is secreted by the mammary glands of the cow, that affect the suitability of milk to support good growth by starter bacteria. Some of these relate to chemical composition, and others to the biological activity of milk. Differences in the chemical composition of milk during the course of lactation affect starter growth and activity only slightly, while the latter factor (biological activity) will occasionally seriously hamper the functions of cultures in a product vat. Variations in chemical composition that are of consequence to starter activity relate to salt balance, ash content of milk and instability in protein colloids. Such compositional variations are encountered very early or very late in lactation and also if the udder tissue is infected (mastitis). The biological activity of milk is due to various natural inhibitors that are present in milk. Some of these agents are enzymes and proteinaceous metal ion chelators, while others are specific and non-specific antibodies. Among the antibodies, the agglutinins are important causes of impairment of starter activity. Very early in lactation the milk has a high titer of non-specific antibodies. Milk from mastitic udders also contain abnormally high amounts of antibodies.

In addition to natural compositional and inhibitory factors associated with milk, there are external chemical and biological agents that enter milk, which are inhibitory to starter bacteria. Examples of such chemical agents include antibiotics used in mastitis therapy, and detergent sanitizers like quaternary ammonium compounds. The sole external biological factor that would be detrimental to starter activity is bacteriophage.

Pooled milk drawn from a variety of production conditions and geographical distribution is now being almost exclusively used for dairy manufacturing. This presents a very special problem in cultured product manufacturing, because the vat milk may at times contain inhibitory levels of any one of the factors mentioned in the foregoing paragraphs. With the ever increasing size of cultured product vats, it is necessary to have a rapid screening test for the suitability of vat milk in relation to the activity of specific starter cultures, to avoid wastage, product losses and overtime work schedules.

The present method is a modification of the resazurin or methylene blue reduction test that is commonly used to determine the quality of raw milk as discussed previously. The scientific principle of the method is the same as that of the well known resazurin reduction test, namely, the rate of reduction of the dye is directly proportional to the density and metabolic activity of microorganisms in a given volume of milk. The test is performed under standardized conditions of inoculum, temperature and period of incubation and concentration of the dye. Generally on a weight basis between about 0.00001 and 0.00010 parts dye are used per part of milk.

A frozen culture concentrate of *Streptococcus cremoris* and *Streptococcus lactis* (Fargo$_R$301 Microlife Technics, Inc.) containing about $50 \times 10^9$ cells per ml intended for use in the vat milk was thawed in chlorinated warm water (40°C or 104°F) and diluted 1/100 by adding 1 ml concentrate to 99 ml buffered dilution blank. The dilution reduced the number of bacteria to the range of $10^5$ to $10^8$ cells per ml and thus slowed down the test. The method consisted of the following steps with the ingredients shown in Table I:

TABLE I

| I Tube No. | II Milk Tested | III Tube Designation | IV Contents of The Tube | | V Total Volume in the Tube |
|---|---|---|---|---|---|
| 1 | Control pretested milk | Negative control | (a) (b) (c) | 1.0 ml milk 4.5 ml phosphate buffer 0.5 ml resazurin | 6.0 ml |
| 2 | Control pretested milk | Positive control | (a) (b) (c) (d) | 1.0 ml milk 4.0 ml phosphate buffer 0.5 ml resazurin 0.5 ml diluted culture | 6.0 ml |
| 3 | Vat milk | Control | (a) (b) (c) | 1.0 ml vat milk 4.5 ml phosphate buffer 0.5 ml resazurin | 6.0 ml |
| 4 | Vat milk | Experimental | (a) (b) (c) (d) | 1.0 ml vat milk 4.0 ml phosphate buffer 0.5 ml resazurin 0.5 ml diluted culture | 6.0 ml |

SPECIFIC EMBODIMENT

The following Example 1 illustrates the present invention.

EXAMPLE 1

The materials and supplies used in the method were as follows:

a. A thermostatically controlled water bath held at 32°C (90°F).
b. Small presterilized disposable capped plastic tubes.
c. A test tube rack to hold the tubes in the water bath.
d. Sterilized milk made up by dissolving 10g of Matrix Mother Culture Medium (Galloway-West, Fond du Lac, Wisconsin) or similar pretested milk powder in 90 ml of distilled water (in a 250 ml Erlenmeyer flask) and autoclaving the reconstituted milk at 121°C (250°F) for exactly 10 min. As soon as the steam pressure came down, the milk was removed from the autoclave and cooled in a bath of cold, lightly chlorinated (25 ppm) tap water. Hold in refrigerator until use.
e. Sterile 5.0 ml and 1.0 ml (graduated in 1/10ths) pipets.
f. Resazurin dye solution made up according to instructions given in Section 15.110 (and 15.209) page 180 (and page 184) *Standard Methods for the Examination of Dairy Products*, 13th ed. 1972 (SMEDP).
g. Representative sample of vat milk collected aseptically in a bottle.
h. Sterile phosphate-buffered distilled water made up according to instructions contained in Section 4.56, page 56, of Standard Methods (SMEDP).
i. Starter culture intended for use in the product vat.
j. Color standards for comparison are necessary. The required standards are specified under Section 15.207, page 184, of Standard Methods (SMEDP).

1. First (a) and then (b) under column IV in the Table I were added into the tubes. The cap was inserted and the tube was inverted twice to mix the contents. It was then placed in water bath and tempered for at least 15 minutes.

2. After the 15 min. holding in water bath, (c) was added and then (d) was added. The cap was closed tightly and mixed by inverting twice. All the tubes were lavender-blue at this stage. The tubes were immediately returned to the water bath. The top of the water bath was covered with brown Kraft paper or otherwise shielded to keep light out which can affect the test.

3. The tubes were checked every 30 minutes up to 90 minutes. Comparison was as follows: Tube 1 with tube 2, tube 1 with tube 3, tube 3 with tube 4 and tube 2 with tube 4.

Resazurin is an oxidation-reduction indicator as previously disclosed. Fully oxidized resazurin dye solution has a bluish-lavender color. Progressive reduction of the dye solution results in the change of lavender-blue color through various hues of lavender, dark pink and light pink until the entire color is discharged. In the fully reduced state the dye solution is colorless. This is shown in Table II.

TABLE II

| Tube | Color of tube contents after 90 min. at 32°C |
|---|---|
| 1 | Bluish-lavender (little or no reduction) |
| 2 | White or very light pink (Good reduction) |
| 3 | Bluish-lavender or lavender (very similar to No. 1 but will depend on the microbiol content of vat milk, its heat treatment, etc.) |
| 4 | Should be same as No. 2 if no inhibitors are present. If inhibitors are present, the reduction will be poor |

TABLE II-continued

| Tube | Color of tube contents after 90 min. at 32°C |
|---|---|
| | or slow. Final color not the same as No. 2. |

In a diluted milk containing a suspension of actively metabolizing microorganism(s), resazurin could serve as the final electron acceptor. So the rate of reduction of the dye is directly related to the number of microorganisms in the nutrient solution and their metabolic activity. If the milk can afford good growth and metabolic activity, rapid reduction of the dye will occur. If on the other hand, the milk contained inhibitory substances, the reduction of the dye will be retarded. The magnitude of the retardation will be proportional to the extent of inhibition. The extent of inhibition depends on the type of inhibitors (antibiotics are very inhibitory) and in some cases the concentration of the inhibitor. Antibiotics are very inhibitory even at low concentrations, but bacteriophages may not be inhibitory at low concentrations. In some instances, the extent of inhibition will vary with the susceptibility of the culture to the inhibitor (for example, certain strains of lactic streptococci are more sensitive to agglutinins than others, and certain others are resistant to these antibodies). With certain microorganisms, the rate of dye reduction has no relationship at all to the concentration of bacterial cells, but only to their metabolic activity (for example, even a very high concentration of *Leuconostoc citrovorum* in a milk sample would not exhibit active reduction of resazurin, because these bacteria metabolize very slowly in milk).

The phosphate buffer in the test is mainly used as a diluent to dilute out the reductones in heated milk. This prevents the reduction of the dye color by agents other than the added starter bacteria. Preferably, the buffer is potassium dihydrogen phosphate (pH 7.2) which also provides the proper osmotic conditions in the diluted milk.

Preferably the test amounts are small, between 1 and 10 ml. Greater or lesser amounts can be used; however, they are unnecessary.

The preferred dye is resazurin since it is sensitive in very small amounts and is rapidly reduced. Other oxidation-reduction colorimetric dyes can be used, such as methylene blue, with good result.

The use of the additional negative controls in tube numbers 1 and 3 is optional. Their use is preferred since they provide additional base colors for comparative analysis.

I claim:

1. The method of determining the bacterial fermentation activity of skim milk with dairy starter cultures by using a colorimetric oxidation reduction sensitive dye, which comprises:
   a. providing the colorimetric dye in at least two separate sterile openable and resealable containers with a standard unadulterated sterile milk in one container and a milk to be tested in the other container;
   b. introducing dairy starter cultures of milk fermenting bacteria into the containers in an equivalent amount of at least about $10^5$ cells per ml; and
   c. comparing the color change between the containers, wherein a fermentation defective milk is determined by a failure of the test milk to rapidly undergo the color change in relation to the color change in the standard milk container.

2. The method of claim 1 wherein the dye is resazurin.

3. The method of claim 1 wherein between about $10^5$ and $10^8$ cells per ml of bacteria are used.

4. The method of claim 1 wherein the dye is methylene blue.

5. The method of claim 1 wherein in addition negative controls without bacteria are conducted in two separate containers with the standard test milk and with the skim milk.

6. The method of claim 1 wherein the contents of the containers includes buffered distilled water.

7. The method of claim 6 wherein the buffer is potassium dihydrogen phosphate.

8. The method of claim 1 wherein the volume of the contents of the containers is between 1 and 10 ml each.

9. The method of claim 1 wherein on a weight basis between about 0.00001 and 0.00010 parts dye per part skim milk is used.

10. The method of claim 9 wherein the dye is resazurin.

* * * * *